US011980347B2

(12) United States Patent
DiCarlo et al.

(10) Patent No.: US 11,980,347 B2
(45) Date of Patent: May 14, 2024

(54) COMBINING NEAR-INFRARED INFORMATION WITH COLORED IMAGES IN IMAGE-GUIDED SURGERY

(71) Applicant: INTUITIVE SURGICAL OPERATIONS, INC., Sunnyvale, CA (US)

(72) Inventors: Jeffrey M. DiCarlo, Austin, TX (US); Max J. Trejo, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 527 days.

(21) Appl. No.: 17/311,304

(22) PCT Filed: Dec. 3, 2019

(86) PCT No.: PCT/US2019/064214
§ 371 (c)(1),
(2) Date: Jun. 4, 2021

(87) PCT Pub. No.: WO2020/117787
PCT Pub. Date: Jun. 11, 2020

(65) Prior Publication Data
US 2022/0015616 A1 Jan. 20, 2022

Related U.S. Application Data

(60) Provisional application No. 62/775,462, filed on Dec. 5, 2018.

(51) Int. Cl.
*A61B 1/04* (2006.01)
*A61B 1/00* (2006.01)
(Continued)

(52) U.S. Cl.
CPC ........ *A61B 1/043* (2013.01); *A61B 1/000094* (2022.02); *A61B 1/00045* (2013.01);
(Continued)

(58) Field of Classification Search
CPC ... A61B 1/043; A61B 1/000094; A61B 1/046; A61B 1/00045; A61B 1/05;
(Continued)

(56) References Cited

U.S. PATENT DOCUMENTS 7,102,142 B2  9/2006 Sendai
7,115,841 B2  10/2006 Zeng et al.
(Continued)

FOREIGN PATENT DOCUMENTS

CN  1489446 A  4/2004
JP  2004008230 A  1/2004

OTHER PUBLICATIONS

Office Action for Chinese Application No. CN201980079973.X, dated Nov. 14, 2023, 22 pages.
(Continued)

*Primary Examiner* — Gabriel I Garcia

(57) ABSTRACT

The technology described herein can be embodied in a method that includes receiving data representing information captured using a first sensor and a second sensor of a multi-sensor camera. The sensors are configured to capture a surgical scene illuminated by a light source configured to emit wavelengths in the visible spectrum corresponding to sensing capabilities of the first and second sensors, respectively. The method also includes receiving data representing information captured using a third sensor of the multi-sensor camera, the third sensor configured to capture the surgical scene as illuminated by a near-infrared light source, and generating a first visual representation of the surgical scene based on the data representing the information captured using the first and second sensors. The first visual representation is combined with the information captured using the
(Continued)

third sensor to generate a second visual representation, and the second visual representation is presented on a display device.

20 Claims, 7 Drawing Sheets

(51) Int. Cl.
  *A61B 1/05* (2006.01)
  *A61B 1/06* (2006.01)
  *A61B 1/313* (2006.01)
  *G06T 7/00* (2017.01)

(52) U.S. Cl.
  CPC .............. *A61B 1/046* (2022.02); *A61B 1/05* (2013.01); *A61B 1/0638* (2013.01); *A61B 1/0646* (2013.01); *A61B 1/3132* (2013.01); *G06T 7/0014* (2013.01); *G06T 2207/10152* (2013.01)

(58) Field of Classification Search
  CPC ... A61B 1/0638; A61B 1/0646; A61B 1/3132; G06T 7/0014; G06T 2207/10152
  USPC ......................................................... 382/165
  See application file for complete search history.

(56) References Cited

U.S. PATENT DOCUMENTS

| | | | |
|---|---|---|---|
| 10,390,718 B2* | 8/2019 | Chen | A61B 1/3132 |
| 11,045,271 B1* | 6/2021 | Tran | G16H 20/40 |
| 2002/0103439 A1 | 8/2002 | Zeng et al. | |
| 2009/0192349 A1* | 7/2009 | Berguer | A61B 1/043 |
| | | | 600/109 |
| 2010/0262017 A1 | 10/2010 | Frangioni | |
| 2011/0261175 A1 | 10/2011 | Fomitchov et al. | |
| 2014/0179997 A1* | 6/2014 | von Grunberg | A61B 1/313 |
| | | | 600/102 |
| 2018/0125333 A1 | 5/2018 | Zhao et al. | |

OTHER PUBLICATIONS

International Search Report and Written Opinion for Application No. PCT/US2019/064214, dated Mar. 20, 2020, 18 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Preliminary Report on Patentability for Application No. PCT/US2019/064214, dated Jun. 17, 2021, 10 pages.

* cited by examiner

COMBINING NEAR-INFRARED INFORMATION WITH COLORED IMAGES IN IMAGE-GUIDED SURGERY

CROSS-REFERENCE TO RELATED APPLICATION

This application is a National Phase Application under 35 U.S.C. § 371 and claims the benefit of International Patent Application No. PCT/US2019/064214 filed on Dec. 3, 2019, which claims the benefit of U.S. Provisional Application No. 62/775,462 titled "Combining Near-Infrared Information with Colored Images in Image-Guided Surgery," filed on Dec. 5, 2018. The disclosure of the foregoing application is incorporated herein by reference in its entirety.

TECHNICAL FIELD

This disclosure relates to near-infrared (NIR) imaging used in endoscopic surgical systems.

BACKGROUND

Minimally invasive surgical systems are being developed to reduce the trauma experienced by patients undergoing surgical interventions. These systems require only small incisions and surgeons use stick like cameras and instruments to perform the procedure. In addition to reducing trauma, teleoperated systems of this type increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site through a display device. Based on visual feedback received through the display device, the surgeon performs the surgical procedures on the patient by manipulating master control input devices, which in turn control the motion of tele-robotic instruments.

SUMMARY

In one aspect, this document features a method that includes receiving data representing information captured using a first sensor and a second sensor of a multi-sensor camera associated with a surgical device. The first and second sensors are configured to capture a surgical scene that includes biological tissues as illuminated by a light source configured to emit wavelengths in the visible spectrum corresponding to sensing capabilities of the first and second sensors, respectively. The method also includes receiving data representing information captured using a third sensor of the multi-sensor camera, the third sensor configured to capture the surgical scene as illuminated by a near-infrared (NIR) light source, and generating, by one or more processing devices, a first visual representation of the surgical scene based on the data representing the information captured using the first and second sensors. The method further includes combining, by the one or more processing devices, the first visual representation with the information captured using the third sensor to generate a second visual representation of the surgical scene, and presenting the second visual representation of the surgical scene on a display device associated with the surgical device.

In another aspect, this document features a method that includes receiving data representing information captured using a first sensor and a second sensor of a camera having at least three sensors, associated with a surgical device. The first and second sensors are configured to capture a surgical scene that includes biological tissues as illuminated by a first source and a second source configured to emit wavelengths in the visible spectrum corresponding to sensing capabilities of the first and second sensors, respectively. The method also includes estimating, by one or more processing devices using the data representing the information captured using the first and second sensors, data representing information expected to be captured by a third sensor upon illumination of the surgical scene by a third source configured to emit wavelengths in the visible spectrum corresponding to sensing capabilities of the third sensor. The method further includes generating a visual representation of the surgical scene using (i) the data representing the information captured using the first and second sensors, and (ii) the predicted data representing the information expected to be captured by the third sensor upon illumination of the surgical scene by the third source, and presenting the visual representation of the surgical scene on a display device associated with the surgical device.

In another aspect, this document features an imaging system that includes an image generator implemented using one or more processing devices. The imaging system is configured to receive data representing information captured using a first sensor and a second sensor of a multi-sensor camera associated with a surgical device, the first and second sensors configured to capture a surgical scene comprising biological tissues as illuminated by a light source configured to emit wavelengths in the visible spectrum corresponding to sensing capabilities of the first and second sensors, respectively. The image generator is also configured to receive data representing information captured using a third sensor of the multi-sensor camera, the third sensor configured to capture the surgical scene as illuminated by a near-infrared (NIR) light source. The image generator is further configured to generate a first visual representation of the surgical scene based on the data representing the information captured using the first and second sensors, combine the first visual representation with the information captured using the third sensor to generate a second visual representation of the surgical scene, and cause presentation of the second visual representation of the surgical scene on a display device associated with the surgical device.

In another aspect, this document features an imaging system that includes an image generator implemented using one or more processing devices. The image generator is configured to receive data representing information captured using a first sensor and a second sensor of a camera having at least three sensors, associated with a surgical device, the first and second sensors configured to capture a surgical scene comprising biological tissues as illuminated by a first source and a second source configured to emit wavelengths in the visible spectrum corresponding to sensing capabilities of the first and second sensors, respectively. The image generator is also configured to estimate, using the data representing the information captured using the first and second sensors, data representing information expected to be captured by a third sensor upon illumination of the surgical scene by a third source configured to emit wavelengths in the visible spectrum corresponding to sensing capabilities of the third sensor. The image generator is further configured to generate a visual representation of the surgical scene using (i) the data representing the information captured using the first and second sensors, and (ii) the predicted data representing the information expected to be captured by the third sensor upon illumination of the surgical scene by the third source, and present the visual representation of the surgical scene on a display device associated with the surgical device.

In another aspect, this document includes one or more machine-readable storage devices having encoded thereon computer readable instructions for causing one or more processing devices to perform various operations. The operations include receiving data representing information captured using a first sensor and a second sensor of a multi-sensor camera associated with a surgical device, the first and second sensors configured to capture a surgical scene comprising biological tissues as illuminated by a light source configured to emit wavelengths in the visible spectrum corresponding to sensing capabilities of the first and second sensors, respectively. The operations also include receiving data representing information captured using a third sensor of the multi-sensor camera, the third sensor configured to capture the surgical scene as illuminated by a near-infrared (NIR) light source, and generating a first visual representation of the surgical scene based on the data representing the information captured using the first and second sensors. The operations further include combining the first visual representation with the information captured using the third sensor to generate a second visual representation of the surgical scene, and presenting the second visual representation of the surgical scene on a display device associated with the surgical device.

In another aspect, this document includes one or more machine-readable storage devices having encoded thereon computer readable instructions for causing one or more processing devices to perform various operations. The operations include receiving data representing information captured using a first sensor and a second sensor of a camera having at least three sensors, associated with a surgical device, the first and second sensors configured to capture a surgical scene comprising biological tissues as illuminated by a first source and a second source configured to emit wavelengths in the visible spectrum corresponding to sensing capabilities of the first and second sensors, respectively. The operations also include estimating, using the data representing the information captured using the first and second sensors, data representing information expected to be captured by a third sensor upon illumination of the surgical scene by a third source configured to emit wavelengths in the visible spectrum corresponding to sensing capabilities of the third sensor, generating a visual representation of the surgical scene using (i) the data representing the information captured using the first and second sensors, and (ii) the predicted data representing the information expected to be captured by the third sensor upon illumination of the surgical scene by the third source, and presenting the visual representation of the surgical scene on a display device associated with the surgical device.

Implementations of the above aspects can include one or more of the following features.

The light source can include a first source and a second source configured to emit the wavelengths corresponding to sensing capabilities of the first and second sensors, respectively, and a third source configured to emit wavelengths corresponding to sensing capabilities of the third sensor. The third source can be deactivated from illuminating the surgical scene. Generating the first visual representation of the surgical scene can include predicting, from the data representing the information captured using the first and second sensors, data representing information expected to be captured by the third sensor upon illumination of the surgical scene by the third source, and generating the first visual representation of the surgical scene from (i) the data representing the information captured using the first and second sensors, and (ii) the predicted data representing the information expected to be captured by the third sensor upon illumination of the surgical scene by the third source. Generating the second visual representation can include determining that the data representing the information captured using the third sensor is indicative of the presence of a fluorescent dye at the surgical scene, and combining (i) the first visual representation and (ii) the data representing the information captured using the third sensor responsive to determining that the data representing the information captured using the third sensor is indicative of the presence of the fluorescent dye. Generating the second visual representation can include generating a desaturated visual representation from the first visual representation, and combining the desaturated visual representation with the data representing the information captured using the third sensor. Generating the desaturated visual representation can include processing the first visual representation using a non-linear color map. The first and second sensors can include filters to pass wavelengths corresponding to red and blue light, respectively. The third sensor can include a filter to pass wavelengths corresponding to green light. User input can be received responsive to presenting the visual representation of the surgical scene on the display device, wherein the user input pertains to operating the surgical device at the surgical scene. The camera can be disposed in the surgical device.

Some or all of the embodiments described herein may provide one or more of the following advantages. One or more sensors of a standard three-sensor camera (e.g., an RGB camera) may be used for capturing NIR images simultaneously with images in the visible range. Using one of the visible range sensors for NIR sensing may obviate the need for a separate NIR sensor, thereby preventing a resolution degradation associated with an additional sensor. Generating an approximation of a full-color visible range image based on a subset of the sensors, and displaying such a full-color image together with an NIR image may allow for visualization of fluorescence without having to switch between a visible range mode and an NIR mode. In some cases, this may allow a surgeon to continue performing surgery while viewing NIR images, thereby potentially improving the value of information gleaned from the NIR images. By adaptively adjusting a color map with the intensity of the detected fluorescence, the color transitions in the displayed representation of the surgical scene may be controlled to prevent display of unnatural colors that could cause confusion for the surgeon.

DETAILED DESCRIPTION

This document describes technology that facilitates concurrent display of NIR images (e.g., images representing fluorescence from a dye such as indocyanine green (ICG)) together with a visible-range image that represents an approximation of a full-color image. The term full-color image, as used in this document, refers to an image captured using a multi-sensor camera (e.g., an RGB camera) under illumination by light in the visible range. The approximate full color images are generated using information captured using a subset of sensors of the multi-sensor camera. In some cases, the technology described herein may facilitate presentation of NIR images concurrently with near full-color visible surgical images (rather than black-and-white images as typically used in NIR imaging), without using specialized camera and/or display devices. In some cases, this may allow a surgeon to continue a surgical procedure while viewing NIR signals in real time, something that may be challenging with black-and-white images. The technology described herein also facilitates a non-linear color mapping that helps in improved visualization of the NIR images when overlaid on the approximate full-color images.

Aspects of the technology are described primarily in terms of an implementation using da Vinci® surgical systems developed by Intuitive Surgical, Inc. of Sunnyvale, California Examples of such surgical systems are the da Vinci® Xi™ Surgical System (Model IS4000). It should be understood that aspects disclosed herein may be embodied and implemented in various ways, including computer-assisted, non-computer-assisted, and hybrid combinations of manual and computer-assisted embodiments and implementations. Implementations on da Vinci® Surgical Systems, e.g. the Model IS4000 are described for illustrative purposes, and are not to be considered as limiting the scope of the inventive aspects disclosed herein. As applicable, inventive aspects may be embodied and implemented in both relatively smaller, hand-held, hand-operated devices and relatively larger systems that have additional mechanical support, as well as in other embodiments of computer-assisted tele-operated medical devices. While the technology is described primarily with reference to an example of a peer-in display, the technology may also be used in other types of wearable or non-wearable display devices such as a head-mounted display device used, for example, in virtual or augmented reality (VR/AR) systems. The images captured may also be displayed on a large format display such as a 3D TV like device or an image projected onto a screen of some kind and viewed by a user wearing glasses which complete the stereo effect by ensuring that the correct image goes to the correct eye. Alternatively, an auto-stereo type display may be used, for example a lenticular based LCD type of display that may also incorporate head and or eye tracking of the viewer (user).

Figure 2:
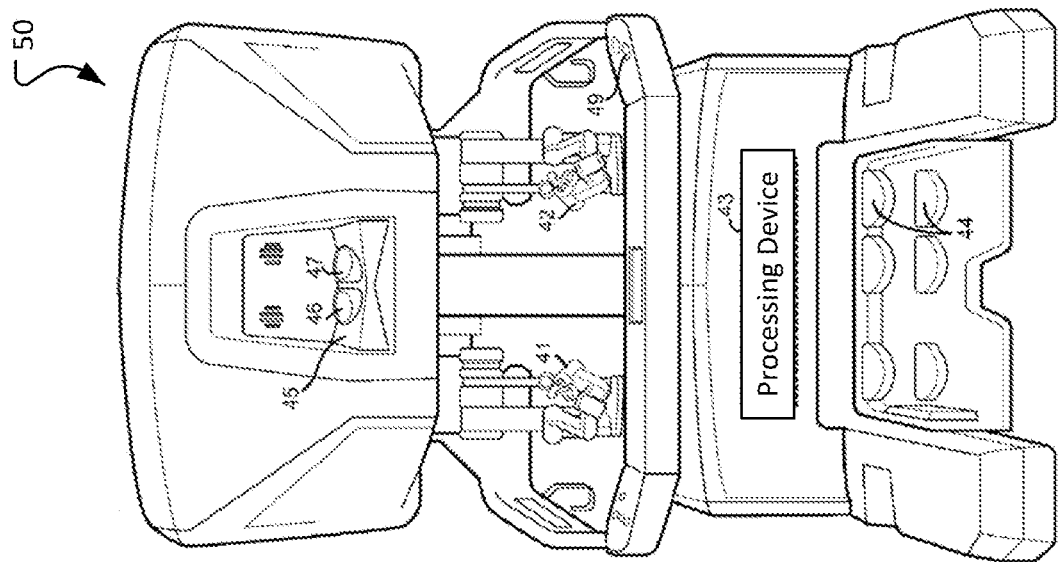
FIG. 2 is a front view of an example surgeon console of a computer-assisted tele-operated surgery system.
Figure 1:
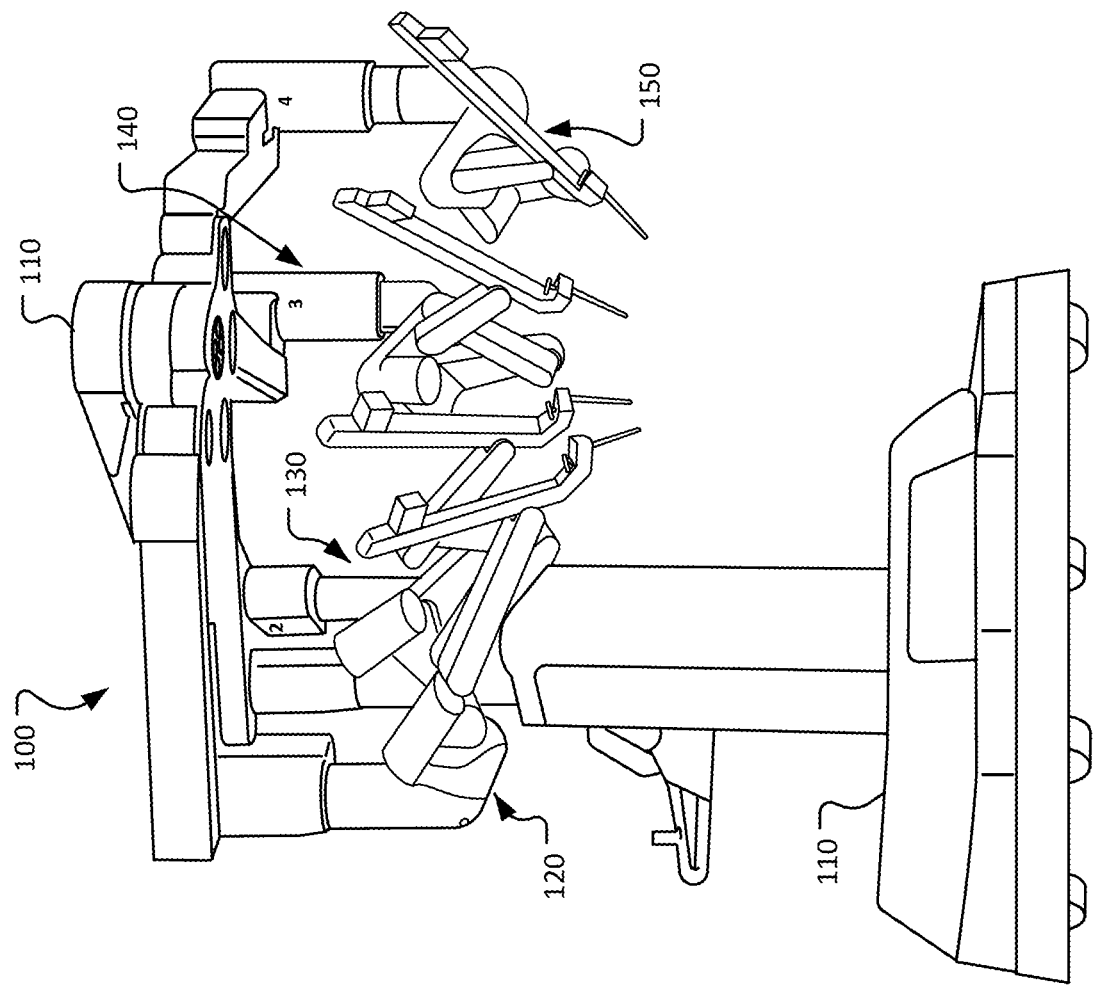
FIG. 1 is a perspective view of an example patient-side cart of a computer-assisted tele-operated surgery system.

Referring to FIGS. 1 and 2, systems for minimally invasive computer-assisted telesurgery (also referred to as MIS) can include a patient-side cart 100 and a surgeon console 50. Telesurgery is a general term for surgical systems where the surgeon uses some form of remote control, e.g., a servomechanism, or the like, to manipulate surgical instrument movements rather than directly holding and moving the instruments by hand. The robotically manipulatable surgical instruments can be inserted through small, minimally invasive surgical apertures to treat tissues at surgical sites within the patient body, avoiding the trauma associated with rather large incisions required for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

In the depicted embodiment, the patient-side cart 100 includes a base 110, a first robotic manipulator arm assembly 120, a second robotic manipulator arm assembly 130, a third robotic manipulator arm assembly 140, and a fourth robotic manipulator arm assembly 150. Each robotic manipulator arm assembly 120, 130, 140, and 150 is pivotably coupled to the base 110. In some embodiments, fewer than four or more than four robotic manipulator arm assemblies may be included as part of the patient-side cart 100. While in the depicted embodiment the base 110 includes casters to allow ease of mobility, in some embodiments the patient-side cart 100 is fixedly mounted to a floor, ceiling, operating table, structural framework, or the like.

In a typical application, two of the robotic manipulator arm assemblies 120, 130, 140, or 150 hold surgical instruments and a third holds a stereo endoscope. The remaining robotic manipulator arm assembly is available so that a third instrument may be introduced at the work site. Alternatively, the remaining robotic manipulator arm assembly may be used for introducing a second endoscope or another image capturing device, such as an ultrasound transducer, to the work site.

Each of the robotic manipulator arm assemblies 120, 130, 140, and 150 is conventionally formed of links that are coupled together and manipulated through actuatable joints. Each of the robotic manipulator arm assemblies 120, 130, 140, and 150 includes a setup arm and a device manipulator. The setup arm positions its held device so that a pivot point occurs at its entry aperture into the patient. The device manipulator may then manipulate its held device so that it may be pivoted about the pivot point, inserted into and retracted out of the entry aperture, and rotated about its shaft axis.

In the depicted embodiment, the surgeon console 50 includes a stereoscopic peer-in display 45 so that the user may view the surgical work site in stereo vision from images captured by the stereoscopic camera used in conjunction with the patient-side cart 100. Left and right eyepieces, 46 and 47, are provided in the stereoscopic peer-in display 45 so that the user may view left and right display screens inside the display 45 respectively with the user's left and right eyes. While viewing typically an image of the surgical site on a suitable viewer or display, the surgeon performs the surgical procedures on the patient by manipulating master control input devices, which in turn control the motion of robotic instruments.

The surgeon console 50 also includes left and right input devices 41, 42 that the user may grasp respectively with his/her left and right hands to manipulate devices (e.g., surgical instruments) being held by the robotic manipulator arm assemblies 120, 130, 140, and 150 of the patient-side cart 100 in preferably six or more degrees-of-freedom ("DOF"). Foot pedals 44 with toe and heel controls are provided on the surgeon console 50 so the user may control movement and/or actuation of devices associated with the foot pedals.

A processing device 43 is provided in the surgeon console 50 for control and other purposes. The processing device 43 performs various functions in the medical robotic system. One function performed by processing device 43 is to translate and transfer the mechanical motion of input devices 41, 42 to actuate their corresponding joints in their associated robotic manipulator arm assemblies 120, 130, 140, and 150 so that the surgeon can effectively manipulate devices, such as the surgical instruments. Another function of the processing device 43 is to implement the methods, cross-coupling control logic, and controllers described herein.

The processing device 43 can include one or more processors, digital signal processors (DSPs), field-programmable gate arrays (FPGAs), and/or microcontrollers, and may be implemented as a combination of hardware, software and/or firmware. Also, its functions as described herein may be performed by one unit or divided up among a number of subunits, each of which may be implemented in turn by any combination of hardware, software and firmware. Further, although being shown as part of or being physically adjacent to the surgeon console 50, the processing device 43 may also be distributed as subunits throughout the telesurgery system. One or more of the subunits may be physically remote (e.g., located on a remote server) to the telesurgery system.

Figure 3:
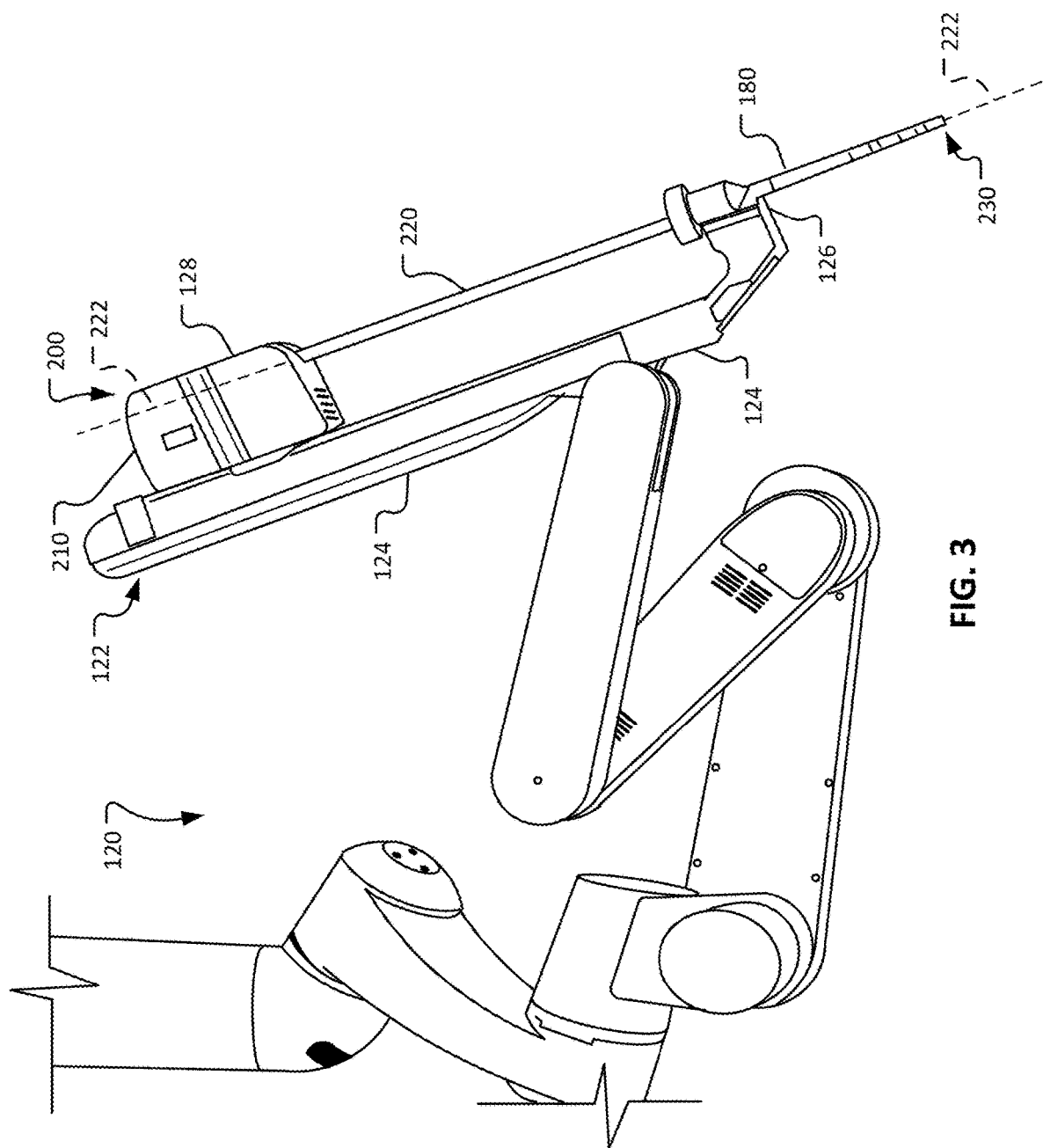
FIG. 3 is a side view of an example robotic manipulator arm assembly of a computer-assisted tele-operated surgery system.

Referring also to FIG. 3, the robotic manipulator arm assemblies 120, 130, 140, and 150 can manipulate devices such as an endoscopic stereo camera and surgical instruments to perform minimally invasive surgery. For example, in the depicted arrangement the robotic manipulator arm assembly 120 is pivotably coupled to an instrument holder 122. A cannula 180 and a surgical instrument 200 are, in turn, releasably coupled to the instrument holder 122. The cannula 180 is a hollow tubular member that is located at the patient interface site during a surgery. The cannula 180 defines a lumen in which an elongated shaft 220 of the endoscopic camera (or endoscope) or surgical instrument 200 is slidably disposed. As described further below, in some embodiments the cannula 180 includes a distal end portion with a body wall retractor member. The instrument holder 122 is pivotably coupled to a distal end of the robotic manipulator arm assembly 120. In some embodiments, the pivotable coupling between the instrument holder 122 and the distal end of robotic manipulator arm assembly 120 is a motorized joint that is actuatable from the surgeon console 50 using the processing device 43.

The instrument holder 122 includes an instrument holder frame 124, a cannula clamp 126, and an instrument holder carriage 128. In the depicted embodiment, the cannula clamp 126 is fixed to a distal end of the instrument holder frame 124. The cannula clamp 126 can be actuated to couple with, or to uncouple from, the cannula 180. The instrument holder carriage 128 is movably coupled to the instrument holder frame 124. More particularly, the instrument holder carriage 128 is linearly translatable along the instrument holder frame 124. In some embodiments, the movement of the instrument holder carriage 128 along the instrument holder frame 124 is a motorized, translational movement that is actuatable/controllable by the processing device 43. The surgical instrument 200 includes a transmission assembly 210, the elongated shaft 220, and an end effector 230. The transmission assembly 210 may be releasably coupled with the instrument holder carriage 128. The shaft 220 extends distally from the transmission assembly 210. The end effector 230 is disposed at a distal end of the shaft 220.

The shaft 220 defines a longitudinal axis 222 that is coincident with a longitudinal axis of the cannula 180. As the instrument holder carriage 128 translates along the instrument holder frame 124, the elongated shaft 220 of the surgical instrument 200 is moved along the longitudinal axis 222. In such a manner, the end effector 230 can be inserted and/or retracted from a surgical workspace within the body of a patient.

Laparoscopic surgery can entail the surgeon viewing the surgical site with the endoscope and performing fine motor manipulations with laparoscopic instruments for exploration, dissection, suturing, and other surgical tasks. These tasks often require fine bi-manual interactions with tissue. In some cases, such bi-manual motor tasks may generally be more easily performed when the surgeon is presented with a 3D view of the surgical scene. The surgical workspace within the body of a patient (the surgical scene) can be presented as a 3D visualization to the surgeon via the stereoscopic display 45. While the technology described herein primarily uses examples of a peer-in stereoscopic display, other types of stereoscopic and non-stereoscopic displays are also within the scope of the technology. A peer-in stereoscopic display refers to a display that allows a user to look into the display without having to wear it or simultaneously share it with another user. A stereo microscope can be an example of a peer-in stereoscopic display. The stereoscopic display 45, as illustrated in FIG. 2 is another example of a peer-in stereoscopic display.

Figure 4:
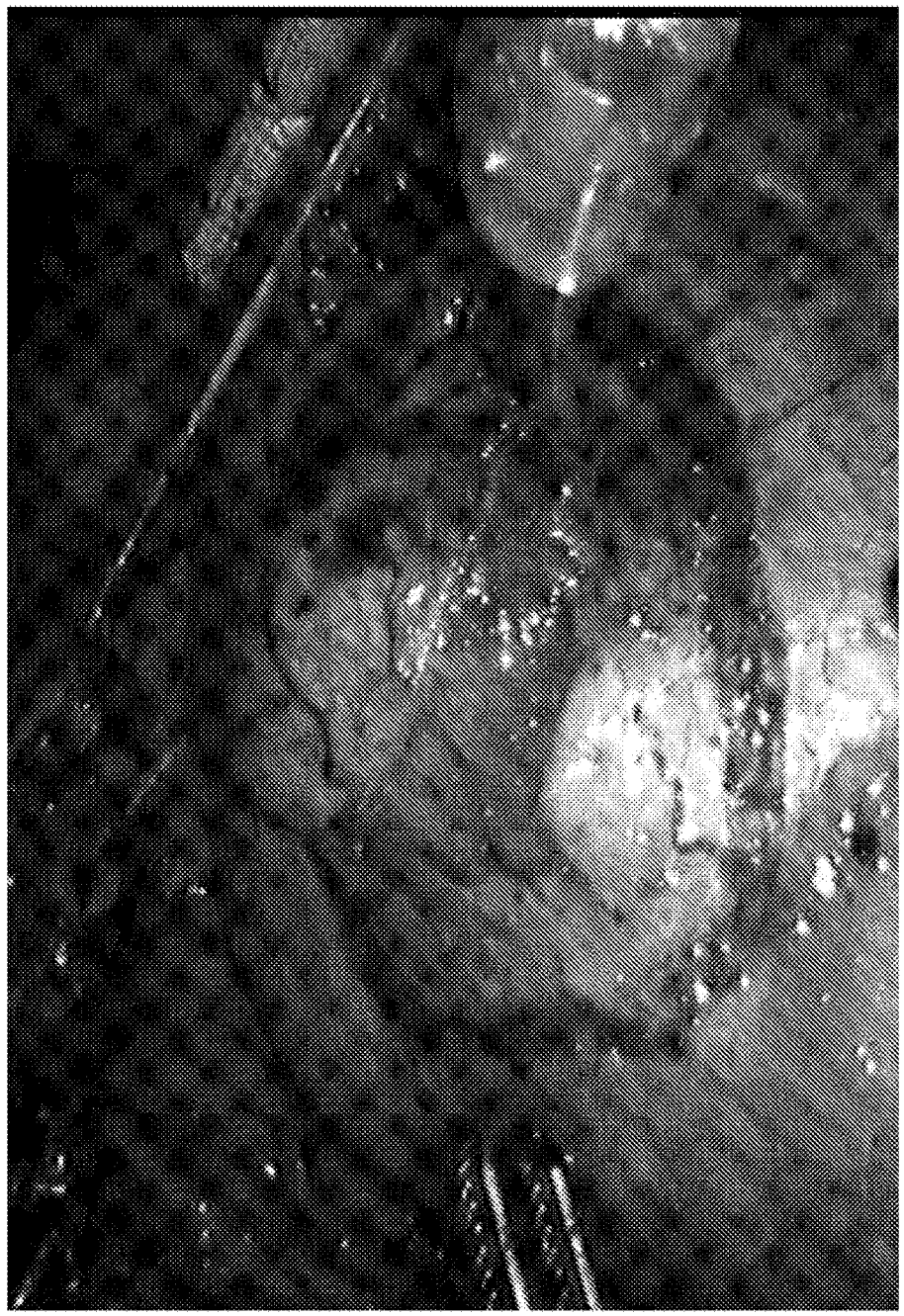
FIG. 4 is an example of a standard near-infrared (NIR) image.

In some implementations, the stereoscopic display 45 can be configured to present NIR images to a surgeon. For this, a dye such as ICG is administered to a patient or subject, and the locations of the dye is imaged under NIR excitation signals. Dyes such as ICG produces a fluorescence, which can be detected under NIR excitation. Presenting NIR images on a display can include generating an image of the corresponding surgical area, and overlaying on it a representation of the fluorescent signal produced by ICG. The image of the surgical area is displayed as a black-and-white image and the fluorescent signal is displayed typically in green on top of the black-and-white image. An example of such an NIR image 400 is illustrated in FIG. 4. While NIR images such as the image 400 is effective in visualizing the locations of ICG in the subject, it is not recommended for a surgeon to operate in this mode because proper visualization of tissue structure may be impaired due to the underlying image being black-and-white. Therefore, the surgeon may have to switch out of an NIR mode into a visible range imaging mode (e.g., a standard white-light mode) to continue operating, but switch back in to the NIR mode for observing the fluorescence, which is not observable in the visible range imaging mode. In some cases, such switching back and forth is time consuming, and does not allow a surgeon to observe the fluorescence in real time when performing the surgical procedure.

Further, implementing NIR imaging alongside visible range imaging may affect spatial resolution or frame rate of the captured images. For example, if a separate NIR sensor is used in a sensor array for sensing the fluorescence, the real estate taken up by the separate NIR sensor affects the spatial resolution of the visible range images. On the other hand, if one of the visible range sensors (e.g., a "green" sensor in an RGB array of sensors) is used for sensing the fluorescence, pulsed illumination alternating between visible light and NIR excitation may be needed. This in turn may cut the frame rate in half. In some cases where global shutters are used with the image sensors, half of the captured frames may be unusable, rendering the effective frame rate to become $1/4^{th}$ of the original frame rate.

The technology described herein stems in part from the realization that for tissues typically encountered at a surgical site when excited using illumination in a certain frequency range, the information captured by some of the sensors or pixels are highly correlated to the information captured by one or more other sensors or pixels. For example, for RGB sensor arrays, the information captured by the green sensors under illumination in the visible range were observed to be highly correlated to the information captured using the blue sensors or pixels. This in turn allows for the green channel information to be predicted from the information captured using the blue sensors. In addition, because the green sensors are also sensitive to NIR excitation, and may not be needed for capturing the green channel information in the visible-range, the green sensors may be used to capture the NIR induced fluorescence concurrently with the visible-range information. Based on the above, the technology described herein allows for capturing visible-range information concurrently with the information representing NIR-induced fluorescence, and generating an approximation of a full-color image of the surgical site by predicting one of the channels (e.g., the green channel for an RGB image) based on the information captured using one or more other sensors (e.g., the blue channel, in this example). The fluorescence signal can then be displayed overlaid on the approximate full-color image, allowing NIR visualization concurrently with a colored image of the surgical site. In some cases, this allows for an improvement in user-experience for the surgeon by obviating the need to switch back and forth between different modes.

Figure 5:
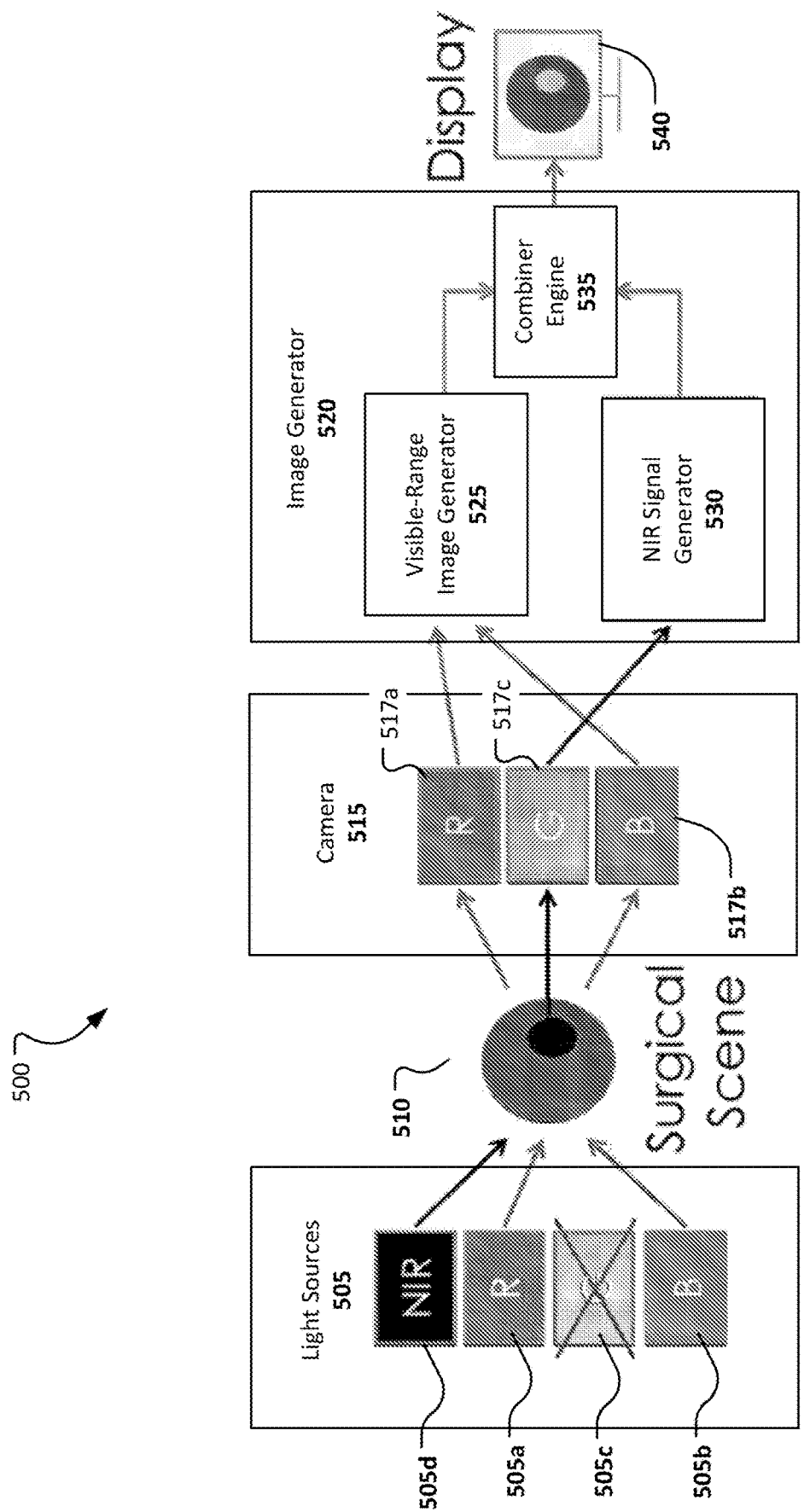
FIG. 5 is a block diagram of an example system for implementing technology described herein.

FIG. 5 is a block diagram of an example system 500 for implementing technology described herein. The system 500 includes light sources 505 that illuminate a surgical scene 510. The light reflected, refracted, or transmitted from the surgical scene 510 is sensed using a multi-sensor camera 515 and provided to an image generator 520. The mage generator includes multiple subparts such as a visible-range image generator 525, a NIR signal generator 530, and a combiner engine 535 that combines the outputs of the visible-range image generator 525 and the NIR signal generator 530. The output of the image generator is provided to a display device 540 that presents a visual representation of the surgical scene 510. In some implementations, the display device 540 is disposed as a portion of the stereoscopic display 45 described above with reference to FIG. 2.

The multi-sensor camera 515 can be of various types. In some implementations, the multi-sensor camera 515 includes a RGB sensor array where sensors for three different wavelength ranges (R sensors for sensing light in the "red" portion of the visible spectrum, G sensors for sensing light in the "green" portion of the visible spectrum, and B sensors for sensing light in the "blue" portion of the visible spectrum) are arranged in a pattern such as a Bayer pattern. In some cases, the entire array is referred to as an image sensor, whereas the individual sensors in the array are referred to as pixels. The pixels corresponding to the R, G, and B sensors can be substantially identical, with the wavelength-specific sensitivities afforded by corresponding color pixels placed over the individual pixels or sensors.

In some implementations, the light sources 505 include multiple sources of electromagnetic energy that excite the surgical scene 510 in wavelength ranges that correspond to the sensors in the multi-sensor camera. For example, in this particular example, the light sources 505 include a first source 505a that emits wavelengths that upon reflection/refraction/transmission from the surgical scene 510 are preferentially sensed by the R sensors 517a. In this example, the light sources 505 also include a second source 505b that emits wavelengths that upon reflection/refraction/transmission from the surgical scene 510 are preferentially sensed by the B sensors 517b. In some implementations, the light sources 505 can also include a third source 505c that emits wavelengths that upon reflection/refraction/transmission from the surgical scene 510 are preferentially sensed by the G sensors 517c. However, in implementations where a channel corresponding to one or the sensors 517 is predicted/estimated using the information in the other channels, the corresponding light source may be omitted (or turned off) from the light sources 505. In this particular example, because the information expected to be captured by the G sensors 517c (upon illumination by a corresponding source 505c) is estimated/predicted from the information captured by the R sensors 517a and the B sensors 517b, the corresponding source 505c is marked with a cross. In some implementations, the Individual light sources 505a, 505b, 505c (505, in general) can include light emitting diodes (LEDs) configured to emit light in the corresponding wavelength ranges.

In some implementations, when anatomical tissues were illuminated using sources in the visible range (e.g., the sources 505a, 505b, and 505c), the information captured using the B sensors 517b (also referred to herein as the blue channel), and the information captured using the G sensors 517c (also referred to herein as the green channel) were observed to be significantly correlated. Such correlation can be observed, for example, when the blue and green channel signals are dominated by blood absorption characteristics. For example, when the signal in the blue channel increases, the signal in the green channel is also likely to increase. Conversely, when the signal in the blue channel decreases, the signal in the green channel is also likely to decrease. In some implementations, the changes in one channel may be substantially proportional to the other. In some implementations, the changes in one channel may have a non-linear relationship with the corresponding changes in the other. In any case, based on this observation for tissue imaging, the underlying correlation can be used to predict/estimate the signal in one channel based on the information in the other correlated channel. In this particular example, the information expected to be sensed by the G sensors 517c is predicted/estimated from the information sensed by the B sensors 517b. Accordingly, the G sensors 517c no longer needs to measure a signal in the visible spectrum. Instead, because the G sensors 517c also exhibit significant sensitivity in the NIR range, such sensitivity can be used to measure a fluorescent signal emitted from a dye (e.g., ICG) in response to being excited by an NIR source 505d.

In some implementations, the light sources 505 are adjusted to support the use of a visible-range sensor for sensing NIR signals. For example, when the G sensors 517c are used for measuring the NIR signal, and the B sensors 517b and R sensors 517a are used for measuring signals in the corresponding ranges in the visible spectrum, the light sources 505 can be adjusted accordingly by turning off the source 505c (e.g., the green-LEDs) so that the G sensors 517c do not pick up any visible green light. Instead, the NIR source 505d is turned on. Under these operating conditions, the B source 505b, the R source 505a, and NIR source 505d illuminate the surgical scene 510 concurrently. Correspondingly, at the multi-sensor camera 515, the information sensed by the B sensors 517 is used to predict the visible green signal, and the fluorescent signal representing locations of the ICG can be extracted from the information sensed by the G sensors 517c.

Once the green signal is predicted from the information sensed by the B sensors 517c, and the fluorescent signal is extracted from the signal sensed by the G sensors 517c, a combined visual representation is generated for presentation to the surgeon, for example, through the stereoscopic display 45. This can be done, for example, at the image generator 520. In some implementations, the image generator 520 can include one or more functional modules or engines, each of which may be implemented as a combination of software and hardware. For example, the image generator 520 can include a visible-range image generator 525 that is configured to generate an approximation of the true full color image. In some implementations, the visible-range image generator 525 is configured to predict the expected information in the green channel by utilizing the correlation with the information in the blue channel (as sensed using the B sensors 517b). The predicted information for the green channel can then be used with the information sensed for the blue and red channels to generate a visual representation that approximates a full color image. In some implementations, when predicting a channel from one or more of the other channels, a level of saturation for the latter channels may be monitored. For example, if one of the channels are saturated over a threshold for certain pixels, those pixels may be masked from being displayed at least because an oversaturated channel may not be reliable for predicting a different channel.

In some implementation, because the R sensors 517a and the B sensors 517b may also detect some NIR signals, the image generator 520 can be configured to preprocess the signals received from the multi-sensor camera 515 to disentangle the NIR information from the R and B channel information. This may be done, for example, using a color transformation matrix that maps the outputs of the sensors 517a and 517b to an output color space where the components due to the NIR excitation are separated. For example, the color transformation matrix can be configured to transform the sensors outputs from a RGB color space to a R'B'NIR color space, where R' and B' represent components of the sensor outputs that are not affected by the NIR excitation. Such a color transformation matrix may be generated, for example, using red and blue illumination only (thereby forcing the output of the green sensor to zero). In some implementations, the output color space can be a polar coordinate based color space such as a YUV color space.

Figures 6A, 6B:
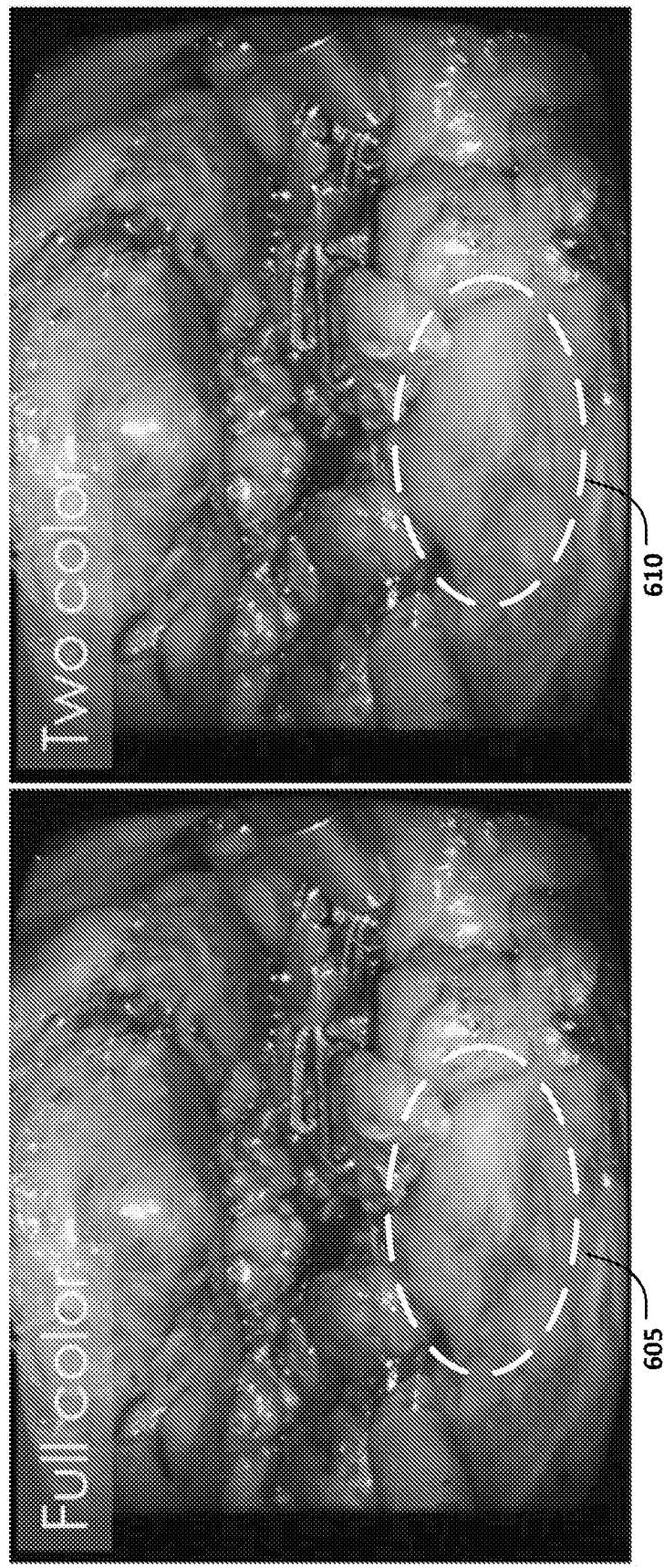
FIGS. 6A and 6B are examples of a full-color image and an image generated using a subset of sensors used in generating the full-color image, respectively.

For the specific type of images in which the green channel information is highly correlated with that of the blue channel, the generated visual representation can closely resemble a full-color image. This is shown using the examples of FIGS. 6A and 6B, which illustrate a full color image, and an approximate full-color image, respectively, of a same surgical scene. In these examples, the approximate full-color image (FIG. 6B) resembles the true full color image (FIG. 6A) closely, and apart from minor differences (as illustrated, for example, by the differences between the areas 605 and 610 in FIGS. 6A and 6B, respectively), are almost identical to one another.

Figure 7:
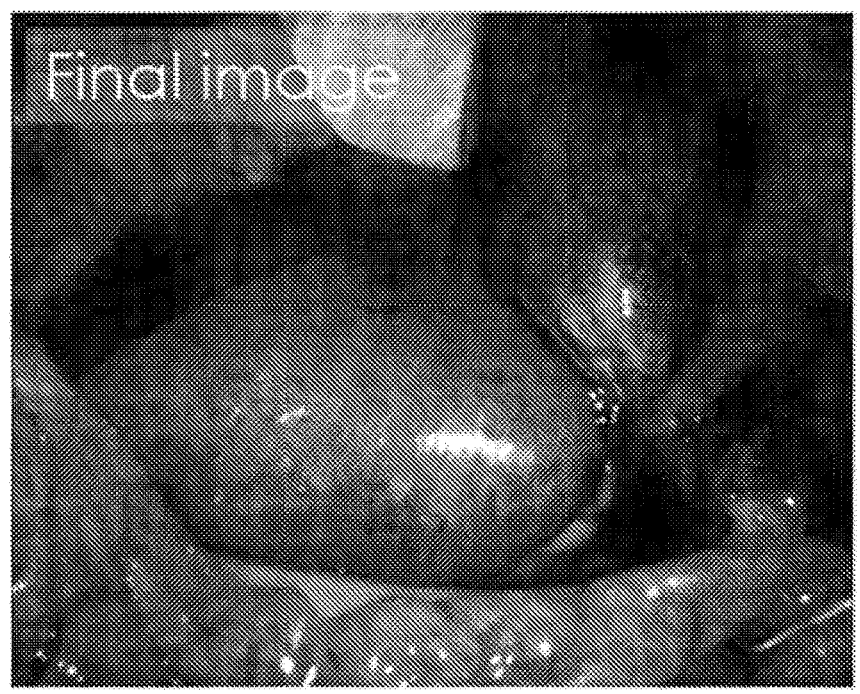
FIG. 7 is an example of a visual representation that combines an NIR image with an approximation of a full-color image.

In some implementations, the approximate full-color image generated using a subset of sensors of the multi-sensor camera 515 can be used as the base image on which the fluorescence information is overlaid. This may be implemented using a NIR signal generator 530 that extracts the fluorescence information from the an output signal of the G sensors 517c, and provides the extracted information to a combiner engine 535 that combines the information with the visual representation generated by the visible-range image generator 525. In some implementation, the NIR signal generator 530 provides information on locations of fluorescence detected by the G sensors 517c, and the combiner engine 535 is configured to overlay a representation of a shade of green on corresponding portions of the approximate full-color visual representation generated by the visible-range image generator 525. The combined visual representation output by the combiner engine 535 is presented on the display device 540. An example of such a combined visual representation is illustrated in FIG. 7, which shows fluorescence related green overlaid on an approximate full color image. Such images, when presented to a surgeon, allows the surgeon to visualize the fluorescence concurrently with colors of the corresponding tissue. In some cases, this may allow the surgeon to continue operating while viewing the fluorescence in real time, and without having to switch to a different mode.

In some implementations, the combiner engine 535 can be configured to execute additional image processing to improve the quality of the visual representation presented to the surgeon. In some cases, simply adding or overlaying shades of green on the approximate full-color image can cause color transitions that make portions of the overall image appear unnatural. For example, a red liver may appear to go from red to orange to yellow to green as the level of green is increased to represent increasing ICG concentrations. In some cases, this may make it challenging to detect low levels of ICG in the liver as the green color may not be visible until the level of ICG reaches a threshold amount. In some implementations, this issue may be addressed using a non-linear color mapping that is triggered upon detection of ICG is detected. In using such a mapping, instead of just adding green to the existing color at the portion where ICG is detected, the existing color is desaturated to black-and-white as green is added. In some implementations, this may prevent confusing color transitions by allowing the corresponding portions to transition from the original color directly to green. For example, a portion of an image representing locations of ICG in the liver can be made to transition from red to green without interim color transitions.

Figure 8:
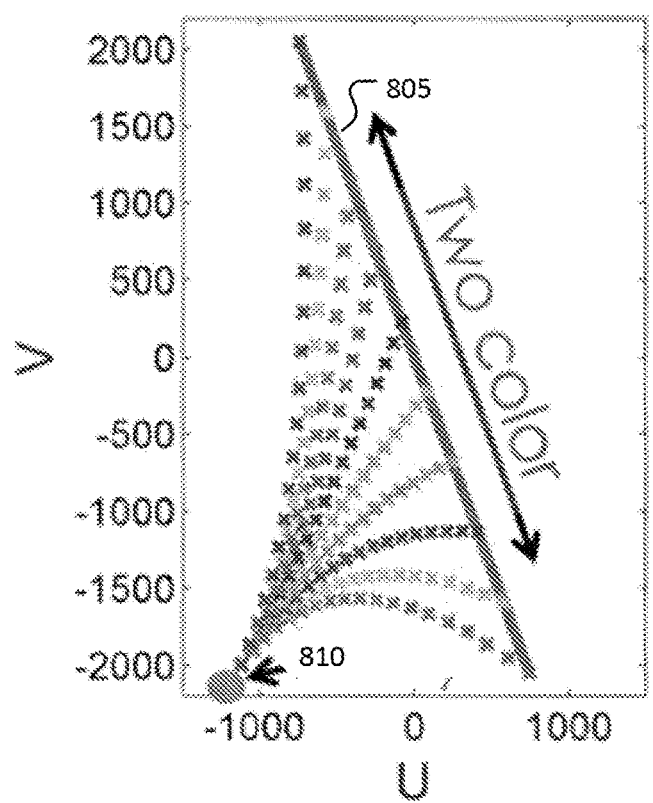
FIG. 8 shows examples of chrominance adjustment trajectories in combining an approximate full-color image with a representation of an NIR image.

In some implementations, the combiner engine 535 can be configured to combine the outputs of the visible-range image generator 525 and the NIR signal generator 530 by adjusting chrominance values of the corresponding visual representations. In some implementations, the luminance values may be left untouched, for example, to prevent reduction in brightness/quality of the final visual representation. FIG. 8 illustrates example trajectories for adjusting chrominance components (UV) of a two color image (or the approximate full-color image as generated by the visible-range image generator 525) in combining the image with a representation 810 of a NIR signal.

Figure 9:
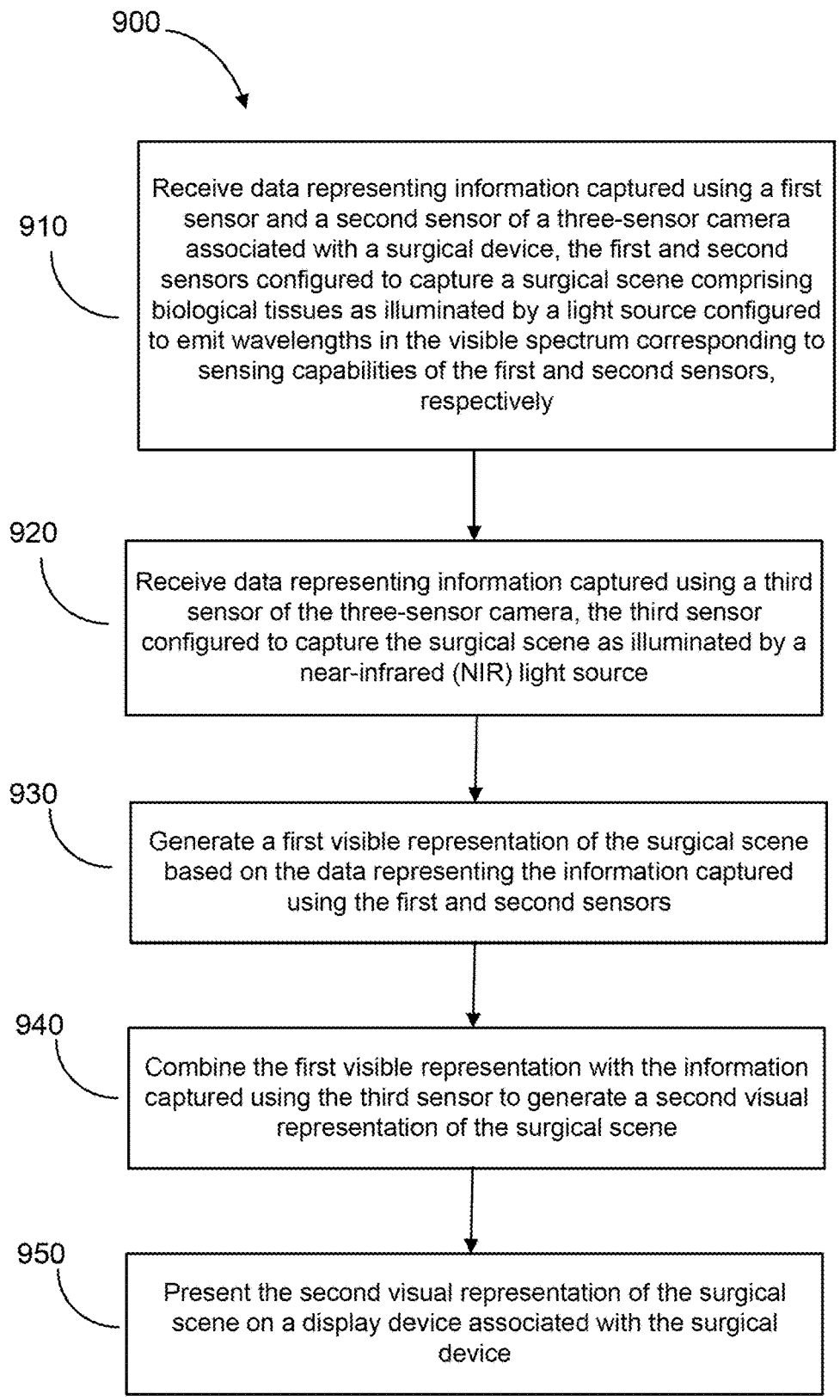
FIG. 9 is a flowchart of an example process for presenting a visual representation that combines an NIR image with an approximation of a full-color image.

FIG. 9 is a flowchart of an example process 900 for presenting a visual representation that combines an NIR image with an approximation of a full-color image. In some implementations, at least a portion of the process 900 may be executed, for example, by one or more processing devices of the image generator 520 described above with reference to FIG. 5. Operations of the process 900 include receiving data representing information captured using a first sensor and a second sensor of a multi-sensor camera associated with a surgical device, the first and second sensors configured to capture a surgical scene comprising biological tissues as illuminated by a light source configured to emit wavelengths in the visible spectrum corresponding to sensing capabilities of the first and second sensors, respectively (910). In some implementations, the first and second sensors can be sensors (e.g. the R sensors 517*a* and B sensors 517*b*, respectively) of the multi-sensor camera 515 described above with reference to FIG. 5. Correspondingly, the light source can include one or more sources 505 also described with reference to FIG. 5. A first source and a second source can be configured to emit the wavelengths corresponding to sensing capabilities of the first and second sensors, respectively. For example, if the first sensor is an R sensor 517*a*, and the second sensor is a B sensor 517*b*, the first source can be configured to emit light in the "red" portion of the visible spectrum, and the second source can be configured to emit light in the "blue" portion of the visible spectrum. In some implementations, a third source can be configured to emit wavelengths corresponding to sensing capabilities of the third sensor. For example, the third source can be substantially similar to the source 505*c* (FIG. 5), which is configured to emit light in the "green" portion of the visible spectrum, corresponding to the sensing capabilities of a G sensor 517*c*.

Operations of the process 900 also include receiving data representing information captured using a third sensor of the multi-sensor camera, the third sensor configured to capture the surgical scene as illuminated by a near-infrared (NIR) light source (920). In some implementations, the light source can include a third source configured to emit wavelengths corresponding to sensing capabilities of the third sensor. For example, the third source can be substantially similar to the source 505*c* (FIG. 5), which is configured to emit light in the "green" portion of the visible spectrum, corresponding to the sensing capabilities of a G sensor 517*c*. However, when the third sensor is used for capturing the surgical scene as illuminated by a NIR source, the corresponding third source may be deactivated from illuminating the surgical scene.

Operations of the process 900 also include generating a first visual representation of the surgical scene based on the data representing the information captured using the first and second sensors (930). This can include, for example, predicting, from the data representing the information captured using the first and second sensors, data representing information expected to be captured by the third sensor upon illumination of the surgical scene by the third source. This also includes, generating the first visual representation of the surgical scene from (i) the data representing the information captured using the first and second sensors, and (ii) the predicted data representing the information expected to be captured by the third sensor upon illumination of the surgical scene by the third source. In some implementations, the data representing information expected to be captured by the third sensor upon illumination of the surgical scene by the third source can represent the green channel information described above, which may be predicted from one or more of the red channel and blue channel information (representing the information captured using the first and second sensors, respectively).

Operations of the process 900 further include combining the first visual representation with the information captured using the third sensor to generate a second visual representation of the surgical scene (940). In some implementations, the third sensor can be substantially similar to a G sensor 517*c* (described above with reference to FIG. 5), which is used to sense a surgical scene as illuminated by a NIR source (e.g., the source 505*d* described with reference to FIG. 5). In some implementations, generating the second visual representation includes determining that the data representing the information captured using the third sensor is indicative of the presence of a fluorescent dye at the surgical scene, and in response, combining (i) the first visual representation and (ii) the data representing the information captured using the third sensor. In some implementations, generating the second visual representation can also include generating a desaturated visual representation from the first visual representation, and combining the desaturated visual representation with the data representing the information captured using the third sensor. Generating the desaturated visual representation can include processing the first visual representation using a non-linear color map.

Operations of the process 900 further include presenting the second visual representation of the surgical scene on a display device associated with the surgical device. In some implementations, the display device can be disposed as a portion of the stereoscopic display 45 described above with reference to FIG. 2. Operations of the process 900 can also include receiving user input responsive to presenting the visual representation of the surgical scene on the display device. Such user input can pertain to operating the surgical device at the surgical scene. For example, the camera is disposed in the surgical device, and based on the visual feedback presented on the display device, a surgeon can manipulate the device to perform a surgical process at the surgical scene.

The functionality of the tele-operated surgery system described herein, or portions thereof, and its various modifications (hereinafter "the functions") can be implemented, at least in part, via a computer program product, e.g., a computer program tangibly embodied in an information carrier, such as one or more non-transitory machine-readable media or storage device, for execution by, or to control the operation of, one or more data processing apparatus, e.g., a programmable processor, a DSP, a microcontroller, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one or more processing devices at one site or distributed across multiple sites and interconnected by a network.

Actions associated with implementing all or part of the functions can be performed by one or more programmable processors or processing devices executing one or more computer programs to perform the functions of the processes described herein. All or part of the functions can be implemented as, special purpose logic circuitry, e.g., an FPGA and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. Components of a computer include a processor for executing instructions and one or more memory devices for storing instructions and data.

While this specification contains many specific implementation details, these should not be construed as limitations on what may be claimed, but rather as descriptions of features that may be specific to particular embodiments. Other embodiments may also be within the scope of the technology described herein. For example, while the technology has been described with reference to RGB sensors, other types of sensors may be within the scope of the disclosure. Also, while the sensors have been described as being arranged in a Bayer pattern, other arrangements are also possible. For example, instead of two G sensors and one each of R and B sensors per set (as in a Bayer pattern), only one each R, G, and B sensors may be used in each set of sensors. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Elements of different implementations described herein may be combined to form other embodiments not specifically set forth above. Elements may be left out of the structures described herein without adversely affecting their operation. Furthermore, various separate elements may be combined into one or more individual elements to perform the functions described herein.

What is claimed is:

1. A method comprising:
    receiving information captured using at least one of a first sensor or a second sensor of a camera having at least three sensors, associated with a surgical device, the first and second sensors configured to capture a surgical scene comprising biological tissues as illuminated by a first source and a second source configured to emit wavelengths in the visible spectrum corresponding to sensing capabilities of the first and second sensors, respectively;
    estimating, by one or more processing devices using the information captured using the at least one of the first or second sensors, information expected to be captured by a third sensor upon illumination of the surgical scene by a third source configured to emit wavelengths in the visible spectrum corresponding to sensing capabilities of the third sensor;
    generating a first visual representation of the surgical scene using (i) the information captured using the at least one of the first or second sensors, and (ii) the estimated information expected to be captured by the third sensor upon illumination of the surgical scene by the third source; and
    causing presentation of the first visual representation of the surgical scene on a display device associated with the surgical device.

2. The method of claim 1, further comprising deactivating the third source from illuminating the surgical scene.

3. The method of claim 1, wherein the third sensor is further configured to capture the surgical scene as illuminated by a near-infrared (NIR) light source.

4. The method of claim 3, further comprising:
    generating, by the one or more processing devices, a second visual representation of the surgical scene by combining the first visual representation with information captured using the third sensor; and
    causing presentation of the second visual representation of the surgical scene on the display device associated with the surgical device.

5. The method of claim 4, wherein generating the second visual representation comprises:
    determining that the information captured using the third sensor is indicative of the presence of a fluorescent dye at the surgical scene; and
    combining the first visual representation with the information captured using the third sensor responsive to determining that the information captured using the third sensor is indicative of the presence of the fluorescent dye.

6. The method of claim 4, wherein generating the second visual representation comprises:
    generating a desaturated visual representation from the first visual representation; and
    combining the desaturated visual representation with the information captured using the third sensor.

7. The method of claim 6, wherein generating the desaturated visual representation comprises processing the first visual representation using a non-linear color map.

8. The method of claim 1, wherein the first and second sensors comprise filters to pass wavelengths corresponding to red and blue light, respectively.

9. The method of claim 1, wherein the third sensor comprises a filter to pass wavelengths corresponding to green light.

10. The method of claim 1, further comprising receiving user input responsive to causing presentation of the first visual representation of the surgical scene on the display device, wherein the user input pertains to operating the surgical device at the surgical scene.

11. The method of claim 1, wherein the camera is disposed in the surgical device.

12. An imaging system comprising:
    an image generator comprising one or more processing devices, the image generator configured to:
        receive information captured using at least one of a first sensor or a second sensor of a camera having at least three sensors, associated with a surgical device, the first and second sensors configured to capture a surgical scene comprising biological tissues as illuminated by a first source and a second source configured to emit wavelengths in the visible spectrum corresponding to sensing capabilities of the first and second sensors, respectively,
        estimate, using the information captured using the at least one of the first or second sensors, information expected to be captured by a third sensor upon illumination of the surgical scene by a third source configured to emit wavelengths in the visible spectrum corresponding to sensing capabilities of the third sensor,
        generate a first visual representation of the surgical scene using (i) the information captured using the at least one of the first or second sensors, and (ii) the estimated information expected to be captured by the third sensor upon illumination of the surgical scene by the third source, and
        cause presentation of the first visual representation of the surgical scene on a display device associated with the surgical device.

13. The imaging system of claim 12 wherein the third sensor is further configured to capture information relating to the surgical scene as illuminated by a near-infrared (NIR) light source.

14. The imaging system of claim 13, wherein the image generator is further configured to:

generate a second visual representation of the surgical scene by combining, by the one or more processing devices, the first visual representation with information captured using the third sensor, and cause presentation of the second visual representation of the surgical scene on the display device associated with the surgical device.

15. The imaging system of claim 14, wherein generating the second visual representation comprises:

determining that the information captured using the third sensor is indicative of the presence of a fluorescent dye at the surgical scene; and combining the first visual representation with the information captured using the third sensor responsive to determining that the information captured using the third sensor is indicative of the presence of the fluorescent dye.

16. The imaging system of claim 14, wherein generating the second visual representation comprises:

generating a desaturated visual representation from the first visual representation; and combining the desaturated visual representation with the information captured using the third sensor.

17. The imaging system of claim 16, wherein generating the desaturated visual representation comprises processing the first visual representation using a non-linear color map.

18. The imaging system of claim 12, comprising a controller configured to deactivate the third source from illuminating the surgical scene.

19. The imaging system of claim 12 wherein the first and second sensors comprise filters to pass wavelengths corresponding to red and blue light, respectively and wherein the third sensor comprises a filter to pass wavelengths corresponding to green light.

20. One or more machine-readable storage devices having encoded thereon computer readable instructions for causing one or more processing devices to perform operations comprising:

receiving information captured using at least one of a first sensor or a second sensor of a camera having at least three sensors, associated with a surgical device, the first and second sensors configured to capture a surgical scene comprising biological tissues as illuminated by a first source and a second source configured to emit wavelengths in the visible spectrum corresponding to sensing capabilities of the first and second sensors, respectively;

estimating, using the information captured using at least one of the first or second sensors, information expected to be captured by a third sensor upon illumination of the surgical scene by a third source configured to emit wavelengths in the visible spectrum corresponding to sensing capabilities of the third sensor; and generating a visual representation of the surgical scene using (i) the information captured using the at least one of the first or second sensors, and (ii) the estimated information expected to be captured by the third sensor upon illumination of the surgical scene by the third source; and cause presentation of the visual representation of the surgical scene on a display device associated with the surgical device.

* * * * *